US008652407B1

(12) United States Patent
Wilson et al.

(10) Patent No.: US 8,652,407 B1
(45) Date of Patent: Feb. 18, 2014

(54) SELF-CONTAINED ASSAY DEVICE

(71) Applicant: PalmStat Diagnostics, LLC, Philadelphia, PA (US)

(72) Inventors: Pete Wilson, Killingworth, CT (US); Eric Butt, Orange, CT (US); Vincent Mata, Monroe, CT (US)

(73) Assignee: PalmStat Diagnostics, LLC, Philadelphia, PA (US)

( * ) Notice: Subject to any disclaimer, the term of this patent is extended or adjusted under 35 U.S.C. 154(b) by 0 days.

(21) Appl. No.: 13/673,541

(22) Filed: Nov. 9, 2012

(51) Int. Cl.
*G01N 33/483* (2006.01)

(52) U.S. Cl.
USPC .............. 422/63; 422/64; 422/510; 422/68.1; 436/518; 436/45; 73/864

(58) Field of Classification Search
USPC ...................................................... 422/63, 64
See application file for complete search history.

(56) References Cited

U.S. PATENT DOCUMENTS

| | | | |
|---|---|---|---|
| 4,385,115 | A | 5/1983 | de Zabala et al. |
| 4,690,801 | A | 9/1987 | Anderson |
| 4,853,335 | A | 8/1989 | Olsen et al. |
| 5,149,505 | A | 9/1992 | English et al. |
| 5,242,803 | A | 9/1993 | Burtis et al. |
| 5,425,921 | A | 6/1995 | Coakley et al. |
| 5,817,522 | A | 10/1998 | Goodman et al. |
| 6,120,733 | A | 9/2000 | Goodman et al. |
| 6,300,142 | B1 | 10/2001 | Andrewes et al. |
| 2004/0002085 | A1 | 1/2004 | Schembri et al. |
| 2010/0028204 | A1 | 2/2010 | Lee et al. |

*Primary Examiner* — Melanie Y Brown
*Assistant Examiner* — Rebecca Martinez
(74) *Attorney, Agent, or Firm* — Stradley Ronon Stevens & Young, LLP

(57) ABSTRACT

A self-contained assay device that is capable of detecting various analyte(s), including bioanalytes, in specimens for example, from biological sources.

18 Claims, 17 Drawing Sheets

SELF-CONTAINED ASSAY DEVICE

STATEMENT REGARDING FEDERALLY SPONSORED RESEARCH OR DEVELOPMENT

The United States Government has rights in this invention pursuant to NIH Grant Number R43AI096558.

FIELD OF THE INVENTION

The present invention relates generally to a self-contained assay device, which is capable of detecting various analytes, including bioanalytes, in specimens, for example, from biological sources. More particularly, the present invention relates to a self-contained disposable assay device for a rapid and convenient detection of analyte(s) by the use of a specific binding pair, such as antibody/antigen, polynucleotide/complementary polynucleotide, ligand/receptor, enzyme/substrate and enzyme/co-factor, etc. The present invention further relates to a method of using the self-contained assay device, either in a hand-held or automated mode.

BACKGROUND OF THE INVENTION

In testing blood or other fluid samples for medical evaluation and diagnosis, a rapid and simple assay is usually needed by medical professionals. Over the years, various devices and methods have been developed for assaying analytes in specimens of biological origin such as, for example, blood and urine.

There still remains a need in the art for a self-contained, inexpensive, disposable assay device for detecting an analyte member of a specific binding pair. More specifically, there is a need for an assay device that can be used easily and effectively by untrained personnel, preferably without the need for complex additional instruments to complete the detection of analyte. The present invention provides such an economical, compact, easy to operate and self-contained assay device for detecting an analyte in a sample, such as a biological sample, which meets the requirements.

SUMMARY OF THE INVENTION

The present invention satisfies this need by providing a self-contained assay device for detecting analyte(s) in a specimen comprising: a first housing having a bottom and a raised wall; a button tower centrally secured to the bottom of the first housing, the button tower including: a base having a spring-loaded ram pin; a button engaging a trigger to retract the ram pin within the base member, the button having a plurality of cut-out portions; a membrane housing block fixedly fit in a position on the raised wall of the first housing and having an opening configured to receive a liquid specimen, the membrane housing block including a porous membrane on a bottom portion, a liquid inlet orifice in a position facing the button tower, and a liquid-tight seal surrounding the opening; an absorbent blotter located adjacent to the bottom of the first housing, the absorbent blotter having a raised portion located in a position under the membrane housing block; a blotter barrier plate located on a surface of the blotter opposite the bottom of the first housing; a second housing adapted to be fixedly fit in the first housing, the second housing including: a top surface having a handle portion and a center hole for receiving the button; a rim portion defining an outer end wall and a plurality of chambers, wherein each chamber has a first opening located at the outer end wall for communicating with the membrane housing block and a second opening located at an inner portion of the chamber opposite the first opening, wherein each chamber has at least one cam-shaped surface adjacent to the second opening, and wherein each chamber has a cylinder and piston assembly secured to the chamber by a coil-over spring, the cylinder and piston assembly retaining a reagent or wash solution, wherein the piston includes a channel comprising a vented set screw, a ball bearing, and a spring acting on the ball bearing to seal an outer end of the channel to provide a liquid-tight reservoir for the reagent or wash solution, wherein, when the button is depressed, the second housing is able to rotate relative to the membrane housing block thus causing the ram pin to engage one of the cam surfaces of the rim portion of the second housing to contain the ram pin until it reaches the second opening in one of the chambers thus causing the ram pin to thrust into the cylinder to move the cylinder and piston assembly, opposite the force of the coil-over spring, against the liquid inlet orifice on the membrane housing block thus moving the ball bearing to break the seal and allow the reagent or wash solution to escape into the membrane housing block and onto the membrane.

In another aspect, the present invention provides a self-contained assay device for detecting analyte(s) in a specimen comprising: a first housing having a bottom and a raised wall; a button tower centrally secured to the bottom of the first housing, the button tower including: a base having a spring-loaded ram pin; a button having a trigger to retract the ram pin within the base, the button having a plurality of cut-out portions; a membrane housing block fixedly fit in a position on the wall of the first housing and having an opening configured to receive a liquid specimen, the membrane housing block including a porous membrane on a bottom portion, a liquid inlet orifice in a position facing the button tower, and a liquid-tight seal surrounding the opening; a second housing adapted to be fixedly fit in the first housing, the second housing including: a top surface having a handle portion and a center hole for receiving the button; a rim portion defining an outer end wall and a plurality of chambers, wherein each chamber has a first opening located at the outer end wall for communicating with the membrane housing block and a second opening located at an inner portion of the chamber opposite the first opening, wherein each chamber has at least one cam-shaped surface adjacent to the second opening, and wherein each chamber has a cylinder and piston assembly secured to the inner bore member by a coil-over spring, the cylinder and piston assembly retaining a reagent or wash solution, wherein the piston includes a channel comprising a vented set screw and a spring acting on a ball bearing to seal an outer end of the channel to provide a liquid-tight reservoir for the reagent or wash solution, wherein, when the button is depressed, the second housing is able to rotate relative to the membrane housing block thus causing the ram pin to engage one of the cam surfaces of the rim portion of the second housing to contain the ram pin until it reaches the second opening in one of the chambers thus causing the ram pin to thrust into the cylinder to move the cylinder and piston assembly, opposite the force of the coil-over spring, against the liquid inlet orifice on the membrane housing block thus moving the ball bearing to break the seal and allow the reagent or wash solution to escape into the membrane housing block and onto the membrane.

In yet another aspect, the present invention provides a method for detecting analyte(s) in a specimen comprising the steps of: adding a specimen of a predetermined quantity into the self-contained assay device as described above through an opening on the second housing; depressing the button and rotating the second housing relative to the membrane housing block causing the ram pin to engage one of the cam surfaces of the rim portion of the second housing to contain the ram pin until it reaches the second opening in one of the chambers thus causing the ram pin to thrust into the cylinder to move the cylinder and piston assembly, opposite the force of the coil-over spring, against the liquid inlet orifice on the membrane housing block thus moving the ball bearing to break the seal and allow the reagent or wash solution to escape into the membrane housing block and onto the membrane; repeating the above step until the ram pin thrusts into a last cylinder and piston assembly to dispense the reagent or wash solution contained therein; and observing the results.

BRIEF DESCRIPTION OF THE DRAWINGS

These and other features, aspects, and advantages of the present invention will become much more apparent from the following description, appended claims, and accompanying drawings, in which:

DETAILED DESCRIPTION OF THE INVENTION

Figure 1:
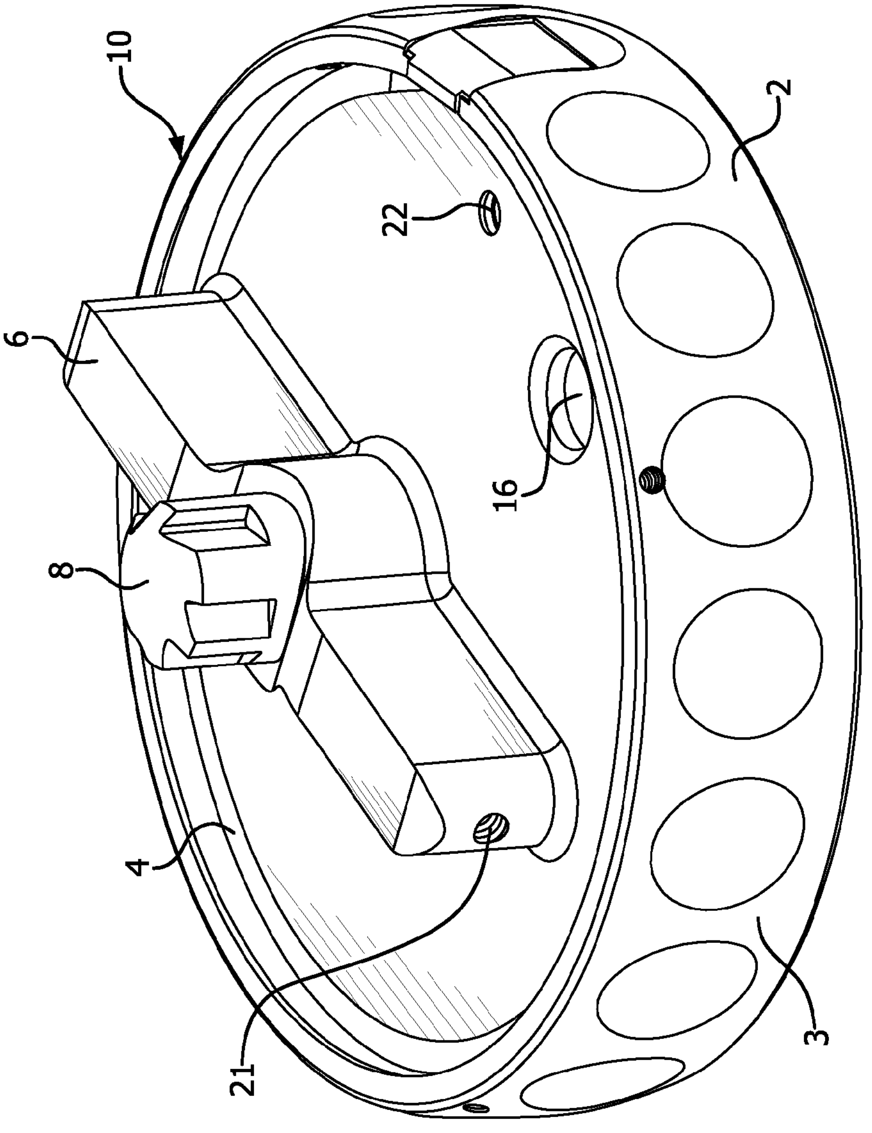
FIG. 1 is a perspective view of an embodiment of the self-contained assay device of the present invention.

Various self-contained assay devices embodying the principles of the present invention are illustrated in FIGS. 1-16. Such self-contained assay devices have a compact structure and are inexpensive to manufacture. Therefore, they can be easily carried for conducting rapid detection of analyte(s) on site. The self-contained assay device can be conveniently discarded after use. In each embodiment, the same elements are designated with the same reference numerals and repetitive descriptions are omitted.

Components of the Device

FIGS. 1 through 16 show multiple features and embodiments of a self-contained assay device 10 of the present invention. Referring to FIG. 1, the assay device 10 has a first housing 2 comprising a raised sidewall 3 and a bottom portion 5. Raised sidewall 3 has a height so that first housing 2 can accommodate a second housing 4 as will be described below. Second housing 4 is tightly fit within the first housing 2.

Figure 2:
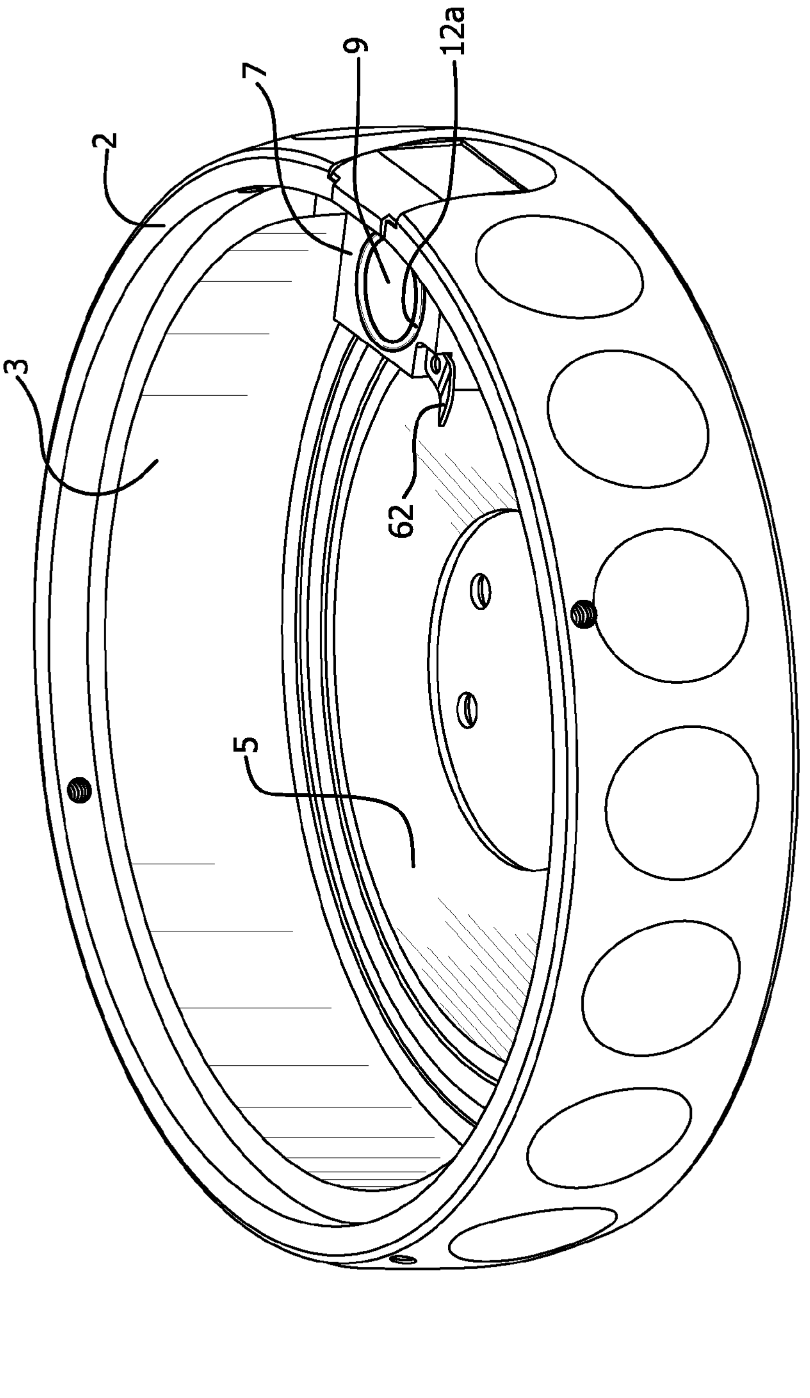
FIG. 2 is a perspective view of an embodiment of the first housing component of the present invention.
Figure 3:
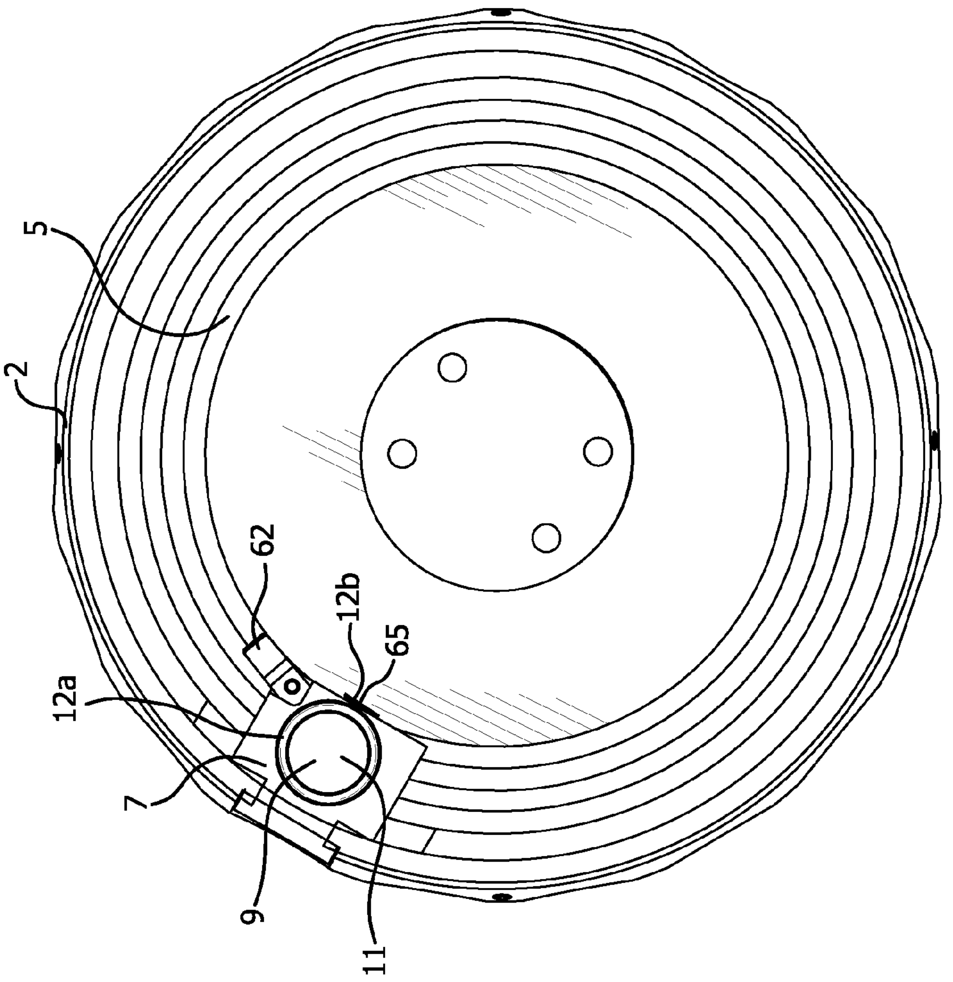
FIG. 3 is a top view of the first housing component of FIG. 2.

As shown in FIG. 2, bottom portion 5 of first housing 2 has a circular shape and thus raised sidewall 3 is also circular. Also attached to first housing 2 is a membrane housing block 7 which, as shown in FIGS. 2 and 3, is in the shape of a rectangular block having a circular chamber 9 housing a membrane 11, which will be described in more detail below. Membrane housing block 7 is shown with an O-ring 12*a* on the upper surface of membrane housing block 7. The function of O-ring 12*a* is to provide a seal between membrane housing block 7 and second housing 4. Membrane 11 can be retained in place through various conventional methods such as adhesion, embedment, insertion, etc. Preferably, membrane housing block 7 is fixedly attached to first housing 2.

Also shown in FIG. 3, membrane housing block 7 also comprises a small O-ring 12*b* on a surface facing a button tower 14 (not shown in FIG. 3) and surrounding a liquid inlet orifice 65. The function of small O-ring 12*b* as well as liquid inlet orifice 65 will be discussed below.

Figure 4:
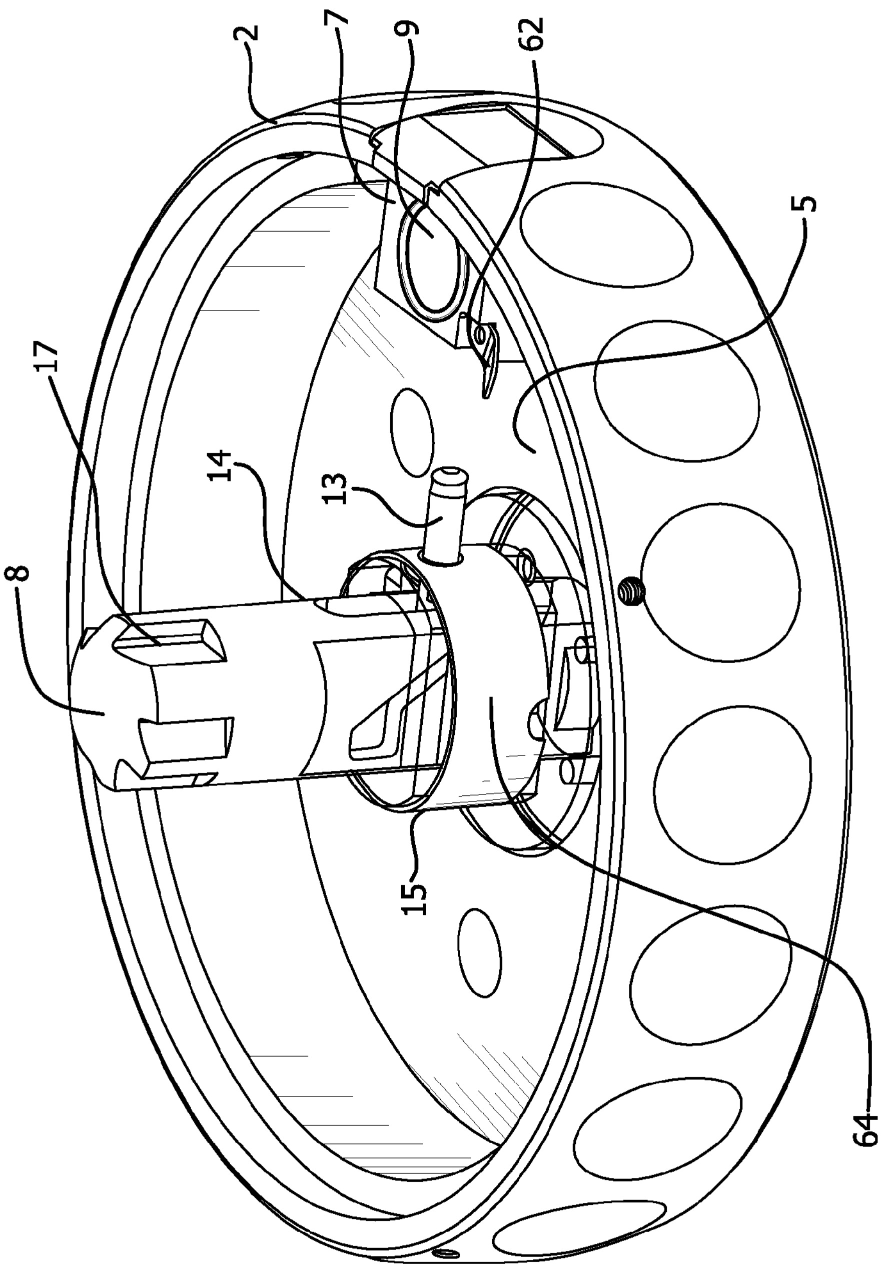
FIG. 4 is a perspective view of an embodiment of the first housing component of the self-contained assay device of the present invention.

As shown in FIG. 4, first housing 2 also comprises button tower 14 comprising a button 8 that, in turn, comprises a plurality of cut-out portions 17 and a base member 15. Base member 15 comprises a retractable ram pin 13, the operation of which will be described in more detail below. Button tower 14 is centrally secured to bottom portion 5 of first housing 2 and remains stationary during operation of assay device 10. Button tower 14 can be secured to first housing 2 by any suitable mechanisms known to those skilled in the art such as, for example, screws, pins, glue, etc. Base member 15 also comprises retaining ring 64 to retain a spring (not shown) that loads ram pin 13.

Figure 5:
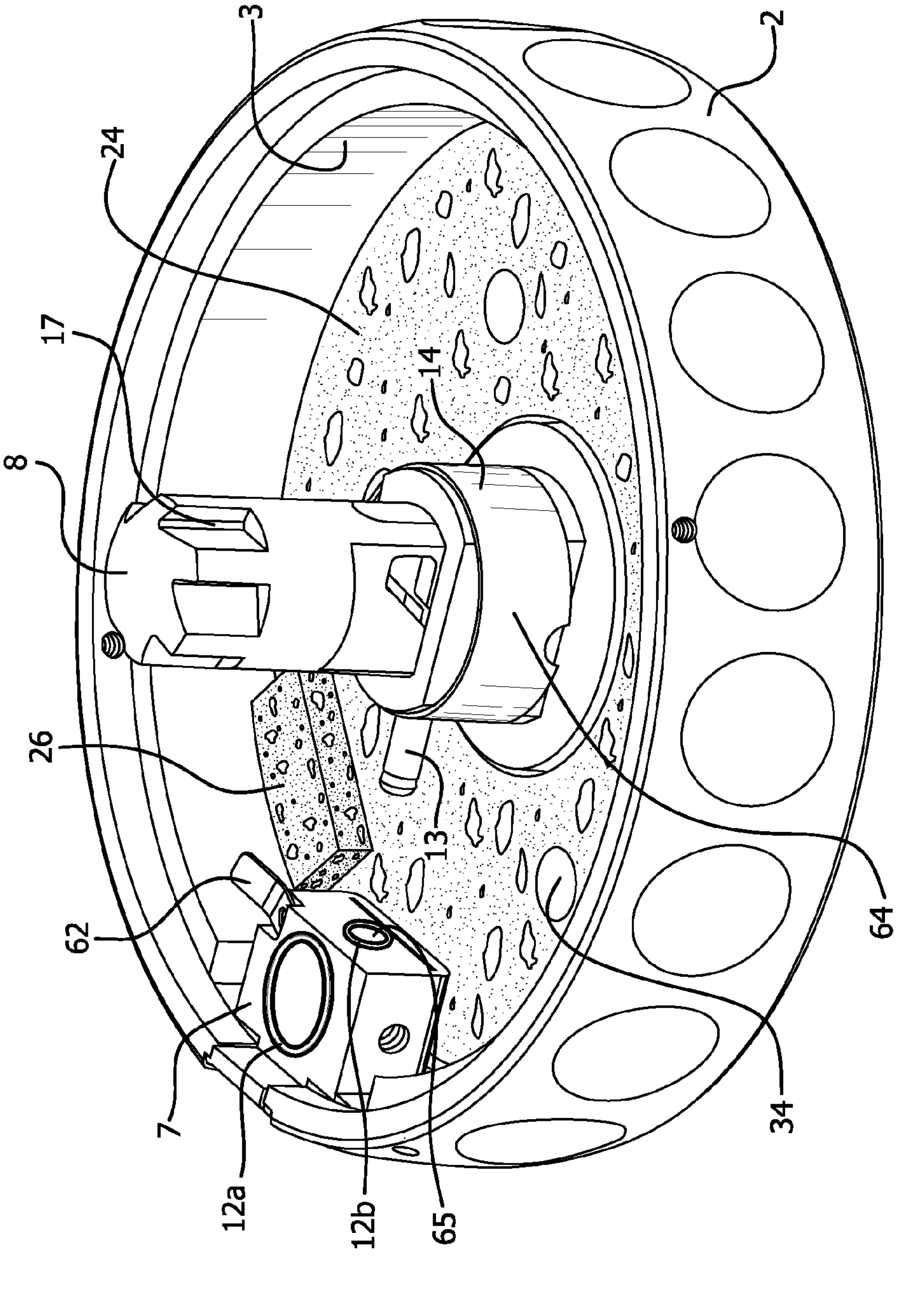
FIG. 5 is a perspective view of an embodiment of the first housing component of the self-contained assay device of the present invention.
Figure 6:
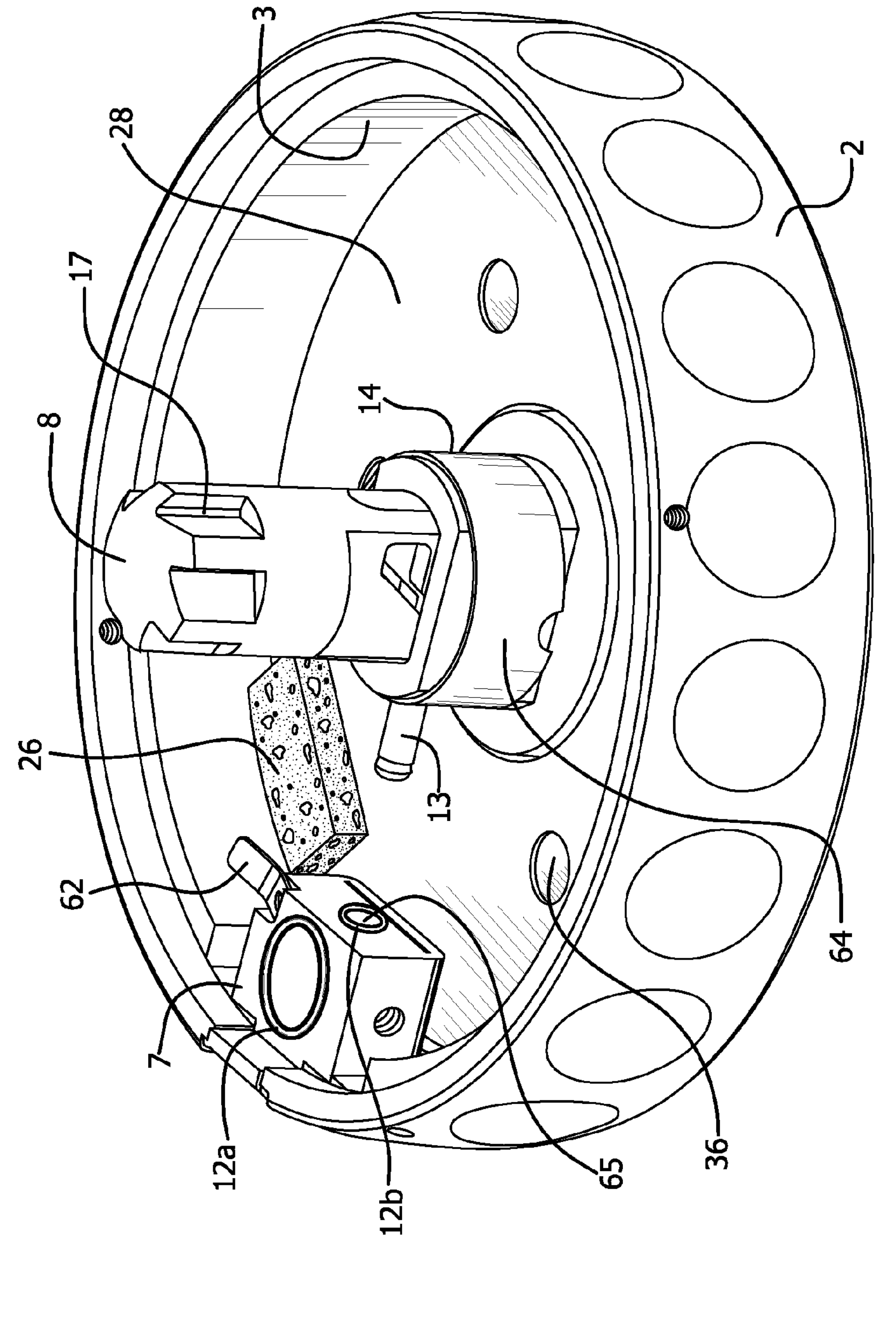
FIG. 6 is a perspective view of an embodiment of the first housing component of the self-contained assay device of the present invention.

Referring to FIGS. 5 and 6, first housing 2, when further assembled, comprises an absorbent blotter 24 located adjacent to bottom portion 5 of first housing 2. Absorbent blotter 24 comprises a raised portion 26 located in a position that, as will be seen below, corresponds to a location underneath membrane housing block 7. Preferably, absorbent blotter 24 is a sponge and is cut around button tower 14. Referring to FIG. 6, a blotter barrier plate 28 is preferably located on a top surface of absorbent blotter 24 opposite bottom portion 5 of first housing 2. The functions of absorbent blotter 24 and blotter barrier plate 28 will be apparent from the description below.

Referring to FIG. 5, absorbent blotter 24 preferably has receiving holes 34 for receiving a corresponding pin (not shown) on second housing 4 as will be described in more detail below. Referring to FIG. 6, blotter barrier plate 28 also has receiving holes 36 that correspond to receiving holes 34 on absorbent blotter 24.

In some embodiments of the present invention (not shown in the Figures), bottom portion 5 of first housing 2 may have at least one hole for sampling large volumes of liquid (e.g., river water) such that the excess volume can pass through bottom portion 5.

First housing 2 of assay device 10 can be made of various materials and by various processes. Materials, such as plastics, are preferred for their inexpensive cost and non-erosive features. In an embodiment, first housing 2 is molded or otherwise fabricated of clear or transparent plastic material. Acrylic is one illustrative non-limiting example of a suitable plastic material. As will be understood by those skilled in the art, any of a number of other polymeric plastic materials are suitable for fabricating assay device 10 of the present invention. One advantage of using such a transparent plastic material is that it is easier for the user to visually observe, with an unaided eye, the elements housed in first housing 2 and to determine whether a chemical reaction or binding has occurred in assay device 10.

Figure 7:
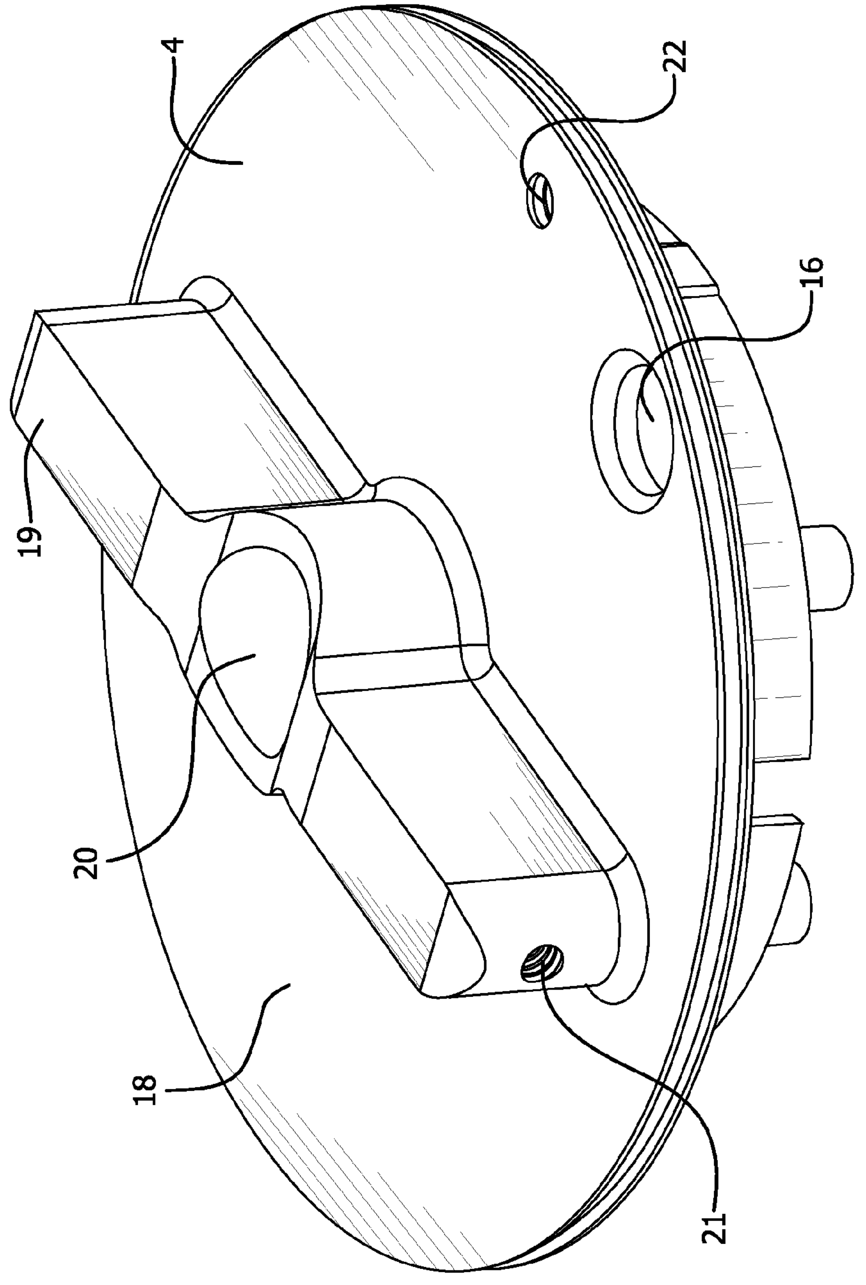
FIG. 7 is a perspective view of an embodiment of the second housing component of the self-contained assay device of the present invention.
Figure 8:
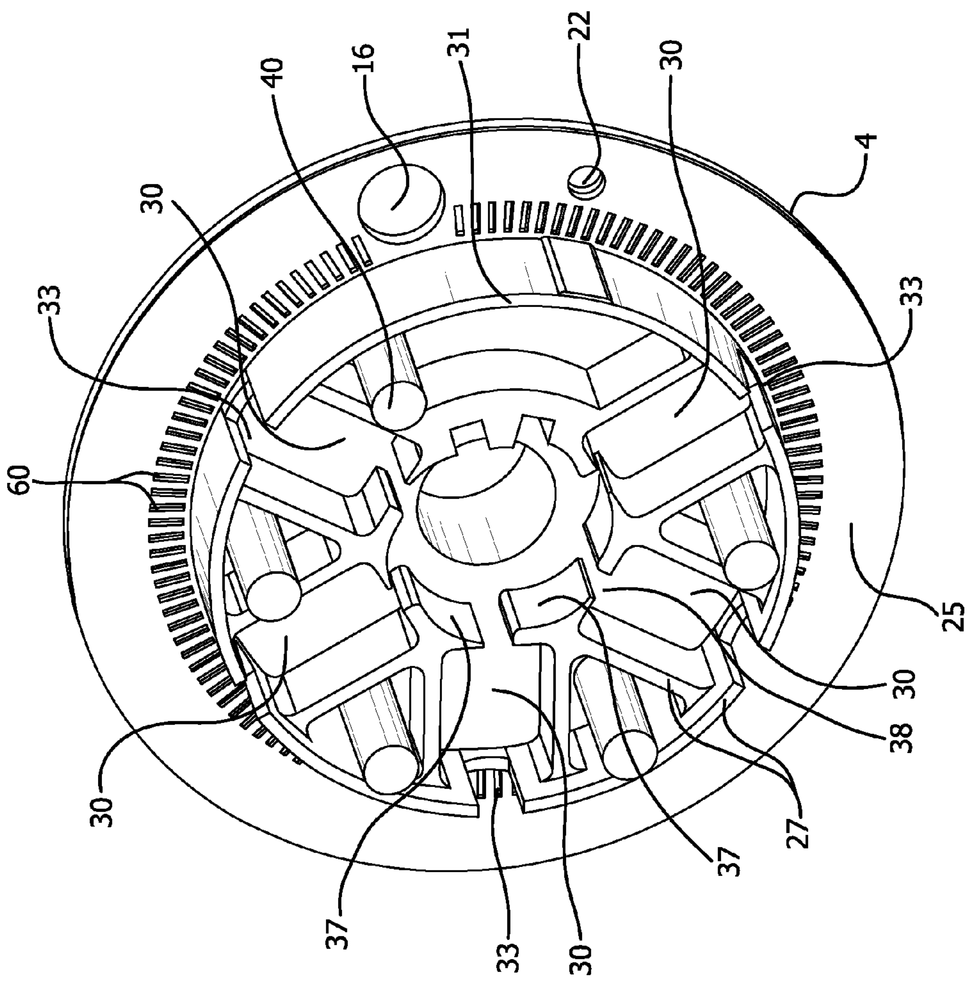
FIG. 8 is a view of the underside of the second housing of the self-contained assay device of the present invention shown in FIG. 7.

Referring now to FIGS. 1, 7, and 8, second housing 4, preferably comprising a cam-plate, is tightly fit within first housing 2 and thus fixed thereto. Second housing 4 is rotatable relative to first housing 2 and membrane housing block 7. Referring to FIG. 7, second housing 4 has a top surface 18 comprising a handle portion 19 and a center hole 20 for receiving the button 8. Handle portion 19 comprises a threaded passage 21 for receiving a spring pin 23 (shown in more detail in FIGS. 12*a*, 12*b*, and 13), the operation of which will be explained below.

Turning now to FIG. 8, the underside of second housing 4 comprises a cam-plate 25 defined by rims 27. Cam-plate 25 is configured as a circular disk made of plastic material, such as clear acrylic, etc. The peripheral of cam-plate 25 is dimensioned to be tightly fit within raised circular sidewall 3 of first housing 2.

Still referring to FIG. 8, rims 27 define an outer end wall 31 and a plurality of chambers 30 for housing a cylinder and piston assembly (not shown) containing a reagent or wash solution. Each chamber 30 has a first opening 33 located at outer end wall 31 for communicating with membrane housing block 7 and a second opening 35 located at an inner portion 38 of chamber 30 opposite first opening 33. First opening 33 is the opening though which the reagent or wash solution is dispensed into membrane housing block 7 and onto membrane 11 via the cylinder and piston assembly which will be described later.

Second opening 35 of each chamber 30 is also defined by rim 27, through which ram pin 13 will thrust into the cylinder and piston assembly in operation as explained in more detail below. Adjacent second opening 35 are portions of rim 27 that define cam surfaces 37. Preferably, at least part of cam surfaces 37 adjacent the second opening 23 of each chamber 30 is curved to facilitate the operation of assay device 10 as will be discussed later.

It is preferred that the plurality of chambers 30 are continuously distributed along, at least a portion of, the periphery of cam plate 25. The number of chambers 30 for self-contained assay device 10 can be up to six or more depending on analysis requirements. In a preferred embodiment shown in FIG. 8, five chambers 30 are provided. Chambers 30 are preferably arranged along the periphery of cam plate 25.

As shown in FIGS. 7 and 8, cam-plate 25 also has an opening 22 located on its rim portion 29, through which a specimen to be tested is introduced into self-contained assay device 10. Opening 22 is preferably aligned with a predetermined start position of assay device 10. In preferred embodiments, opening 22 is also adapted to receive a receptacle (not shown) such as, for example, a syringe.

A filter member can also be provided with assay device 10 to filter particulates such as erythrocytes, aggregates, crystals, etc. from the specimen. In one embodiment, the filter member is affixed to opening 22 on cam-plate 25. In an alternative embodiment, the filter member is designed to be assembled in membrane housing block 7. When a specimen is added into assay device 10 through either opening 22 on cam-plate 25, the filter member can remove debris or the like from the specimen.

Cam-plate 25 can further have an observation port 16 (FIGS. 7 and 8) located on its rim portion 29. Observation port 16 is preferably spaced away from the center of cam-plate 25 for such a distance that it can be aligned with membrane housing block 7. Further, observation port 16 can have a removable cover (not shown) that can be provided to fit in and from the top of observation port 16 to seal the same.

Also shown in FIG. 8 are posts 40 that, when assay device 10 is assembled, fit matingly into receiving holes 34 in blotter 24 as well as corresponding receiving holes 36 of blotter barrier plate 28. This configuration allows absorbent blotter 24 and blotter barrier plate 28 to turn within first housing 2 along with second housing 4 during operation of assay device 10. Such rotation ensures a fresh spot on blotter 24 to absorb liquid reagents or wash solution 43 for each analysis.

Figure 9:
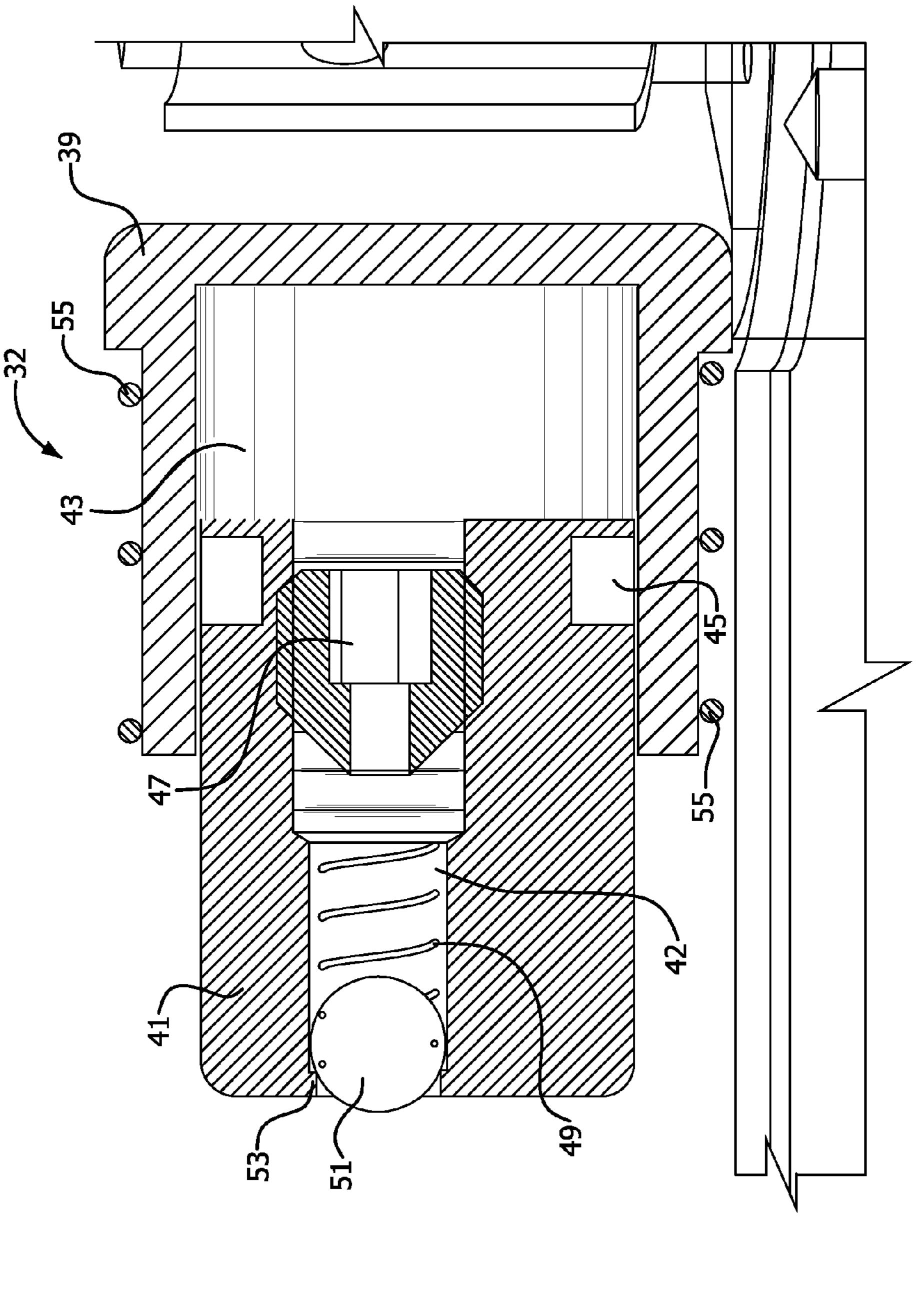
FIG. 9 is a cross-sectional view of an embodiment of a piston and cylinder assembly of the self-contained assay device of the present invention.

Referring now to FIG. 9, a preferred cylinder and piston assembly 32 is shown. Cylinder and piston assembly 32 contains the reagent or wash solution 43 for use with the present invention. The reagent or wash solution 43 will be housed in a cylinder 39 and sealed by an O-ring 45 on a piston 41. Piston 41 comprises a channel 42 there through comprising a vented set screw 47 and a spring 49 acting on a ball bearing 51 to form a seal. In a preferred embodiment, channel 42 is machined in such a way that ball bearing 51 is held against an internal lip 53 by force of spring 49. Thus, when cylinder 39 is filled and piston 41 is inserted into cylinder 39, cylinder and piston assembly 32 becomes a liquid tight reservoir.

Figure 10:
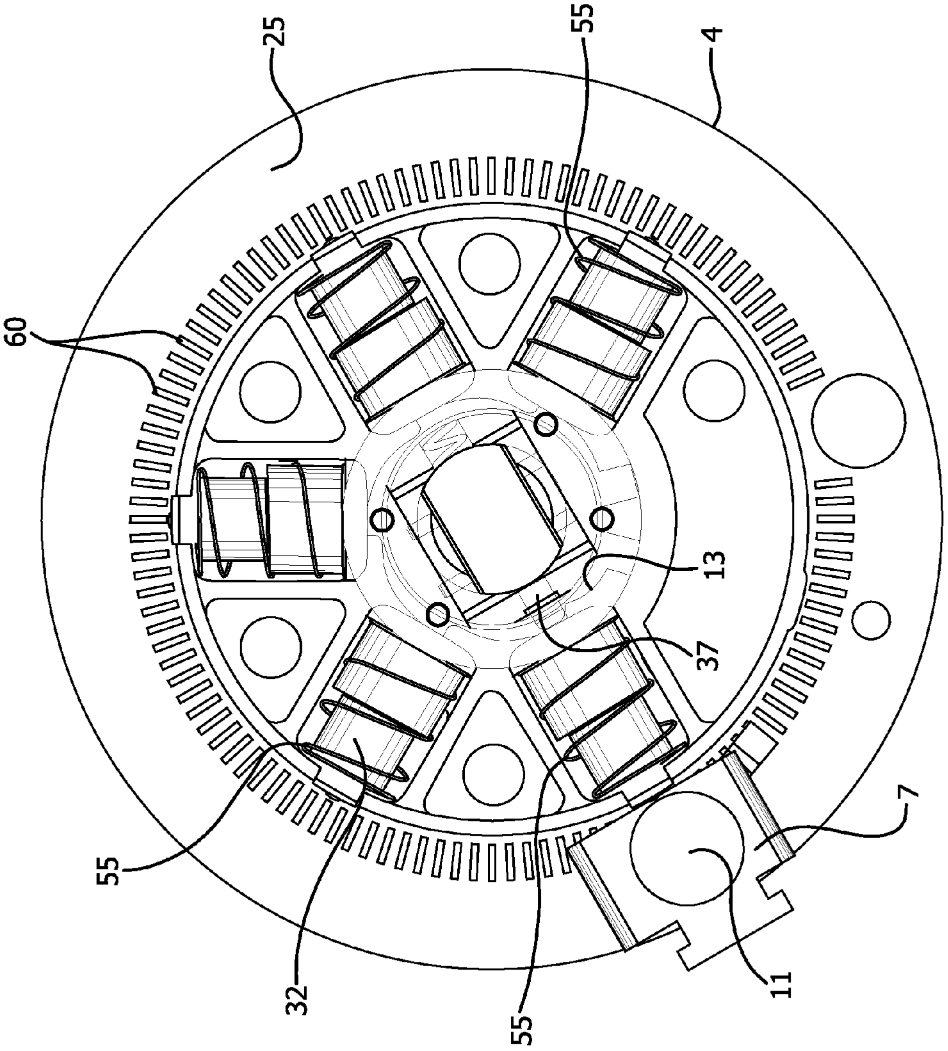
FIG. 10 is a top view of the underside of the second housing component of the self-contained assay device of the present invention shown in FIG. 7 illustrating the piston and cylinder assemblies of FIG. 9 contained therein.

FIG. 10 shows cylinder and piston assemblies 32 in their respective chambers 30 in cam-plate 25. Each cylinder and piston assembly 32 is held in place by a light coil over spring 55. Light coil over spring 55 applies a force on cylinder and piston assembly 32 towards the center of assay device 10.

The Membrane

Membrane 11 is preferably made of a porous material including but not limited to such as nitrocellulose, etc., so unbound specimen or reagent or wash solution is allowed to pass through membrane 11 onto blotter 24 through raised portion 26, while the bound specimen or reagent is immobilized by membrane 11 for subsequent reaction or examination as will be described below.

In certain embodiments of the present invention, membrane 11 can immobilize one member of a specific binding pair, which is complementary to the analyte(s) to be detected, on a portion 59*b* (FIG. 11*a*) of membrane 11 to serve as a "capture site" for any analyte in the specimen. For example, if the analyte to be detected is an antibody, the antigen to which the antibody binds specifically can be immobilized on a predetermined area or zone of portion 59*b* of membrane 11. As another example, if the analyte to be detected is an antigen, an antibody to which the antigen binds specifically can be immobilized on a predetermined area or zone 59*b* of membrane 11.

Further, membrane 11 can be used to immobilize not only the specimen and/or a member of the specific binding pair but also one or more reagents which can serve as a positive or negative control. For a positive control, membrane 11 has a predetermined amount of the analyte(s) to be detected immobilized on a predetermined area or zone of portion 59*b* of membrane 11. For a negative control, membrane 11 has a predetermined amount of a substance to which the analyte does not bind specifically immobilized on a predetermined area or zone of portion 59*b* of membrane 11.

Figure 11A:
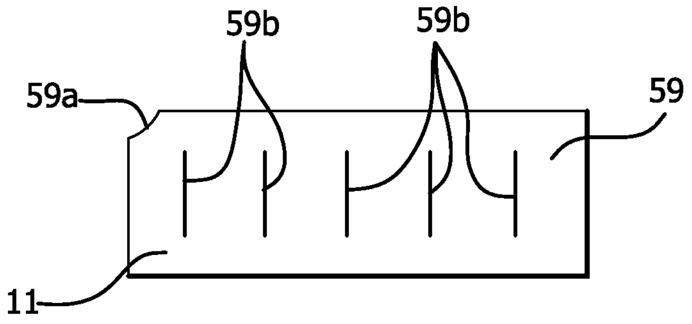
FIGS. 11*a*, 11*b*, and 11*c* show various membranes for use in the self-contained assay device of the present invention.

FIG. 11*a* shows a number of areas or zones for portion 59*b* at which the appropriate substance to serve as a positive or negative control, for example, can be immobilized. The areas or zones of portion 59*b* shown in FIG. 11*a* are presented for illustrative purposes only and, as will be understood by those skilled in the art, the size and configuration of the areas or zones of portion 59*b* is a matter of design choice.

Figure 11B:
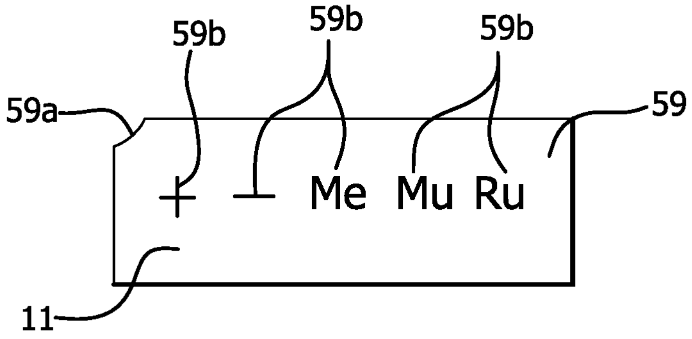

In a preferred embodiment as shown in FIG. 11*b*, the areas and zones 59*b* are configured as signs "+" and "−" and letters "Me," "Mu," and "Ru." These signs and letters represent the different substances bound on the areas and zones of portion 59*b* of membrane 11, such as those used for positive and negative control, measles antigen, mumps antigen and rubella antigen as in an embodiment described hereinafter. Such signs and letters can directly reflect the assay reactions that occur at the areas and zones of portion 59*b* and thereby make it easier for the user to identify or determine which analyte(s) (e.g., antibodies) is or are present in the specimen tested.

Figure 11C:
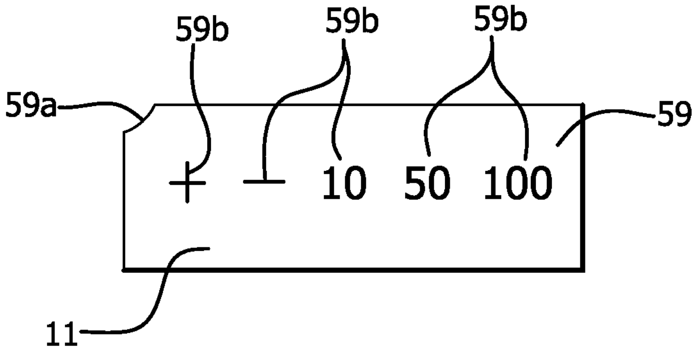

In another preferred embodiment as shown in FIG. 11*c*, the areas and zones of portion 59*b* are configured as signs "+" and "−" and numbers such as "10," "50," and "100." Similar to those in the above embodiment, the signs are to represent the specific substances bound on membrane 11 which are used for positive and negative control. The numbers, on the other hand, are used to represent the amount of the same substance, such as an antigen, bound on the areas and zones of portion 59*b* of membrane 11. Depending on the color change at these areas and zones of portion 59*b* after the assay reaction, the numbers can assist in determining the amount of a specific analyte (e.g., antibody) in the specimen tested.

In addition, the number of areas or zones of portion 59*b* depends upon the number of analytes to be assayed using assay device 10. For example, as shown in FIG. 11*a*, the areas or zones of portion 59*b* can have immobilized positive control reagents for five different assays. Alternatively, the zones or areas of portion 59*b* can have immobilized one substance for a negative control and four positive control reagents. FIG. 11*a* is presented for illustrative purposes only and the determination of the size, number, and configuration of the areas or zones of portion 59*b* are well within the skill in the art.

Additionally, membrane 11 can be configured so that portions 59*b* of membrane 11 can be oriented in a predetermined orientation. In a preferred embodiment, a cut-out portion 59*a* (FIGS. 11*a* to 11*c*) can be provided on membrane 11 so that it can be properly oriented during manufacturing and assembling. Other orientating mechanisms as will be contemplated by those skilled in the art can also be used.

Operation

When assembled, absorbent blotter 24, blotter barrier plate 28, and second housing 4 comprising cam plate 25 and piston and cylinder assemblies 32 comprising reagent or wash solution 43 are all accommodated in first housing 2 with second housing 4 being fixedly fit within first housing 2. Second housing 4 is rotatable relative to first housing 2 and membrane housing block 7 but is retained in a start position through the engagement between receiving holes 34 and 36 with posts 40. In embodiments where housings 2 and 4 are made of non-transparent materials, observation port 16 on second housing 4 is aligned with circular chamber 9 on membrane housing block 7. Fluids comprising various reagent(s) and/or wash solution(s) 43 for the test analysis or analyses are placed and retained in each of piston and cylinder assemblies 32 which are contained in each of chambers 30 of cam plate 25. In one embodiment, a receptacle such as, for example, a syringe (not shown) can be attached to opening 22 on second housing 4 for dispensing a specimen to be tested in assay device 10.

Descriptions will now be made in relation to the operation of the self-contained assay device 10 of the present invention. A sufficient volume of a specimen to be tested is introduced into assay device 10 through opening 22 on second housing 4 so that it covers completely or wets membrane 11 in membrane housing block 7. In other words, the added specimen is deposited on membrane 11. Second housing 4 is then ready to be rotated relative to membrane housing block 7 such that second housing 4 and cam plate 25 leave the start position and move toward the first of chambers 30.

Figure 12A:
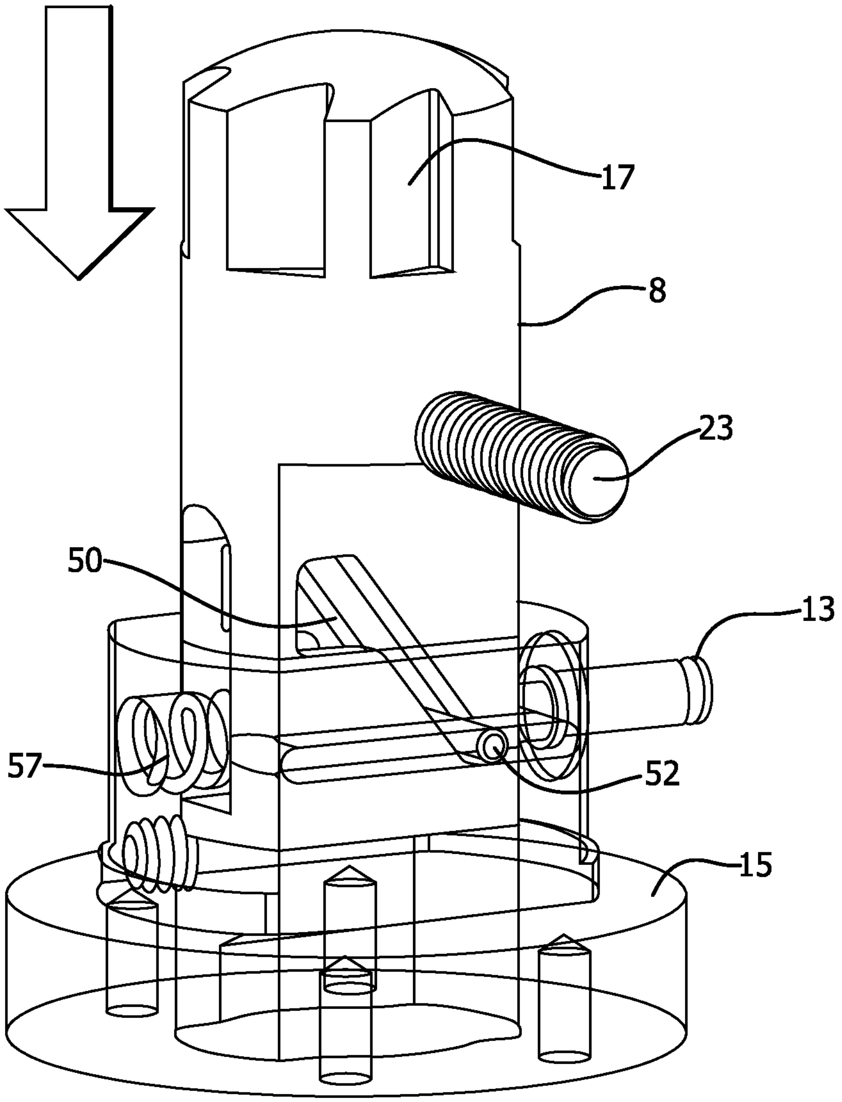
FIGS. 12*a* and 12*b* show side views of the operation of an embodiment of the button tower of the self-contained assay device of the present invention.
Figure 12B:
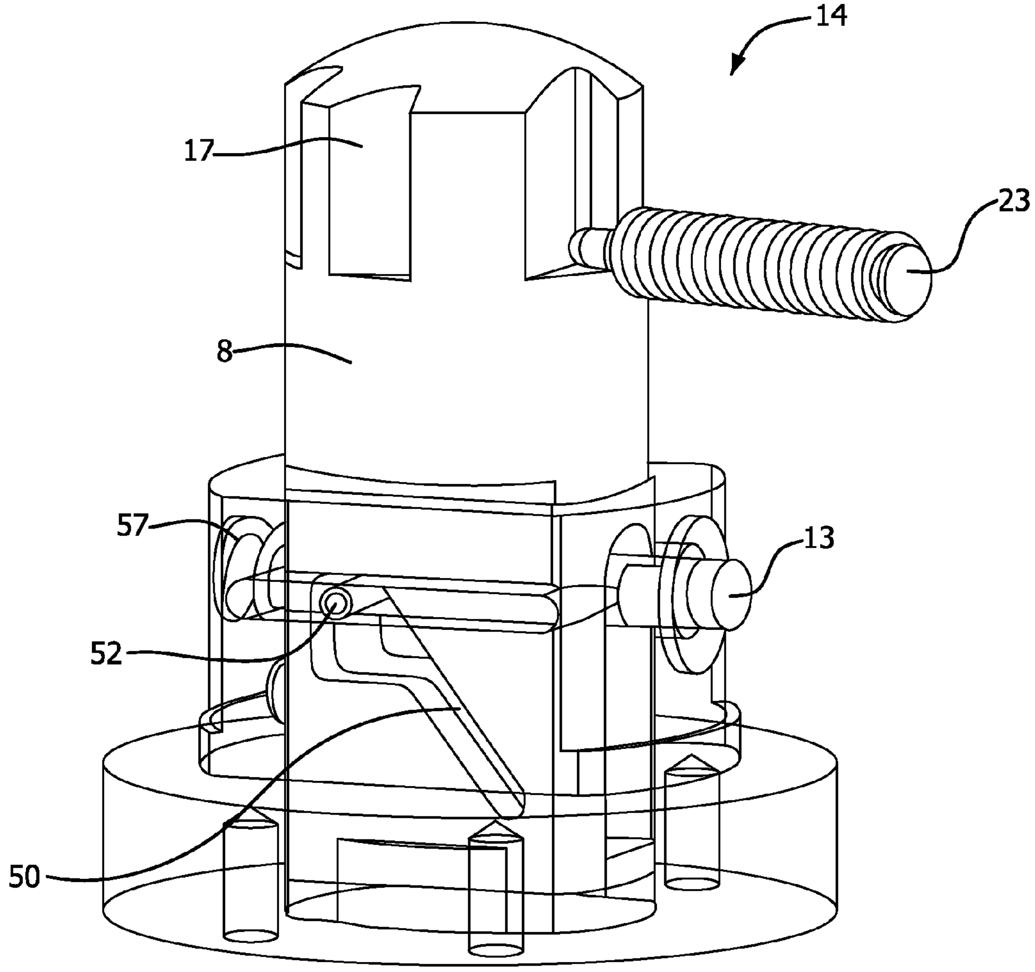
Figure 13:
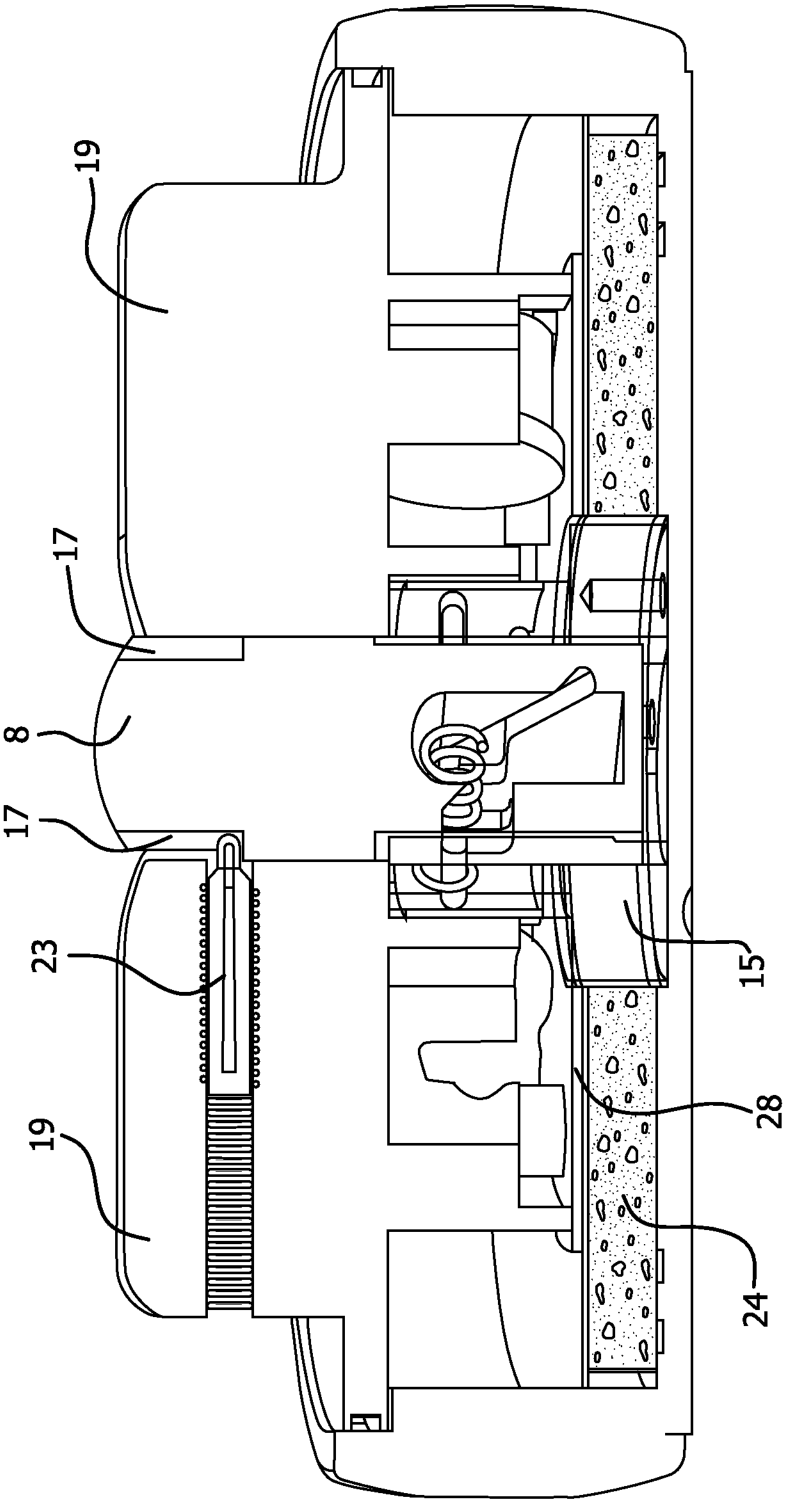
FIG. 13 is a cross-sectional view of an embodiment of the self-contained assay device of the present invention.

Referring to FIGS. 12*a*, 12*b*, and 13 the operation of assay device 10 begins with depressing button 8. Button 8 comprises a trigger to retract retractable ram pin 13 within base member 15 of button tower 14. The trigger acts to retract ram pin 13 against the force of a spring 57 by cooperation of an angled lateral slot 50 with a pin member 52 which is secured transversely to ram pin 13. Spring 57 is preferably secured to retaining ring 64 (not shown in FIGS. 12*a* and 12*b*). In some embodiments of the present invention, a cone spring can also be employed to increase the load on ram pin 13.

Referring to FIGS. 12*b* and 13, as button 8 is depressed, angled lateral slot 50 drives ram pin 13 back against spring 57 and spring pin 23 in handle portion 19 engages one of cut-out portions 17 in button 8 to hold button 8 in the depressed position until second housing 4 is rotated in the clockwise direction. By turning handle portion 19 on second housing 4, the entire second housing 4, which includes cam plate 25 and piston and cylinder assemblies 32, and absorbent blotter 24 and blotter barrier plate 28 rotate. As second housing 2 is rotated, spring pin 23 rolls out of cut-out 17 on button 8 and allows button 8 to reset between stations while simultaneously locking assay device 10 in this position until button 8 is depressed again.

Figure 14:
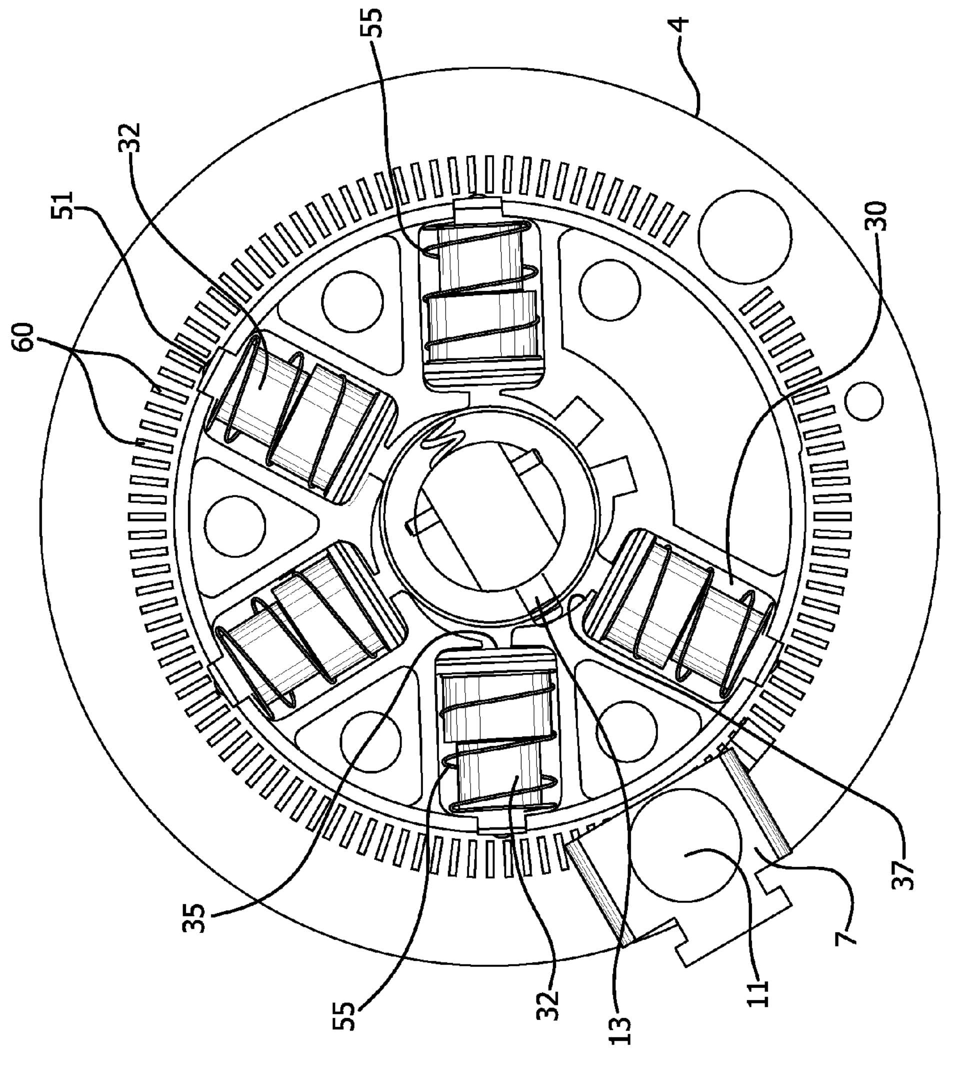
FIG. 14 is a perspective view of the operation of an embodiment of the self-contained assay device of the present invention.
Figure 15:
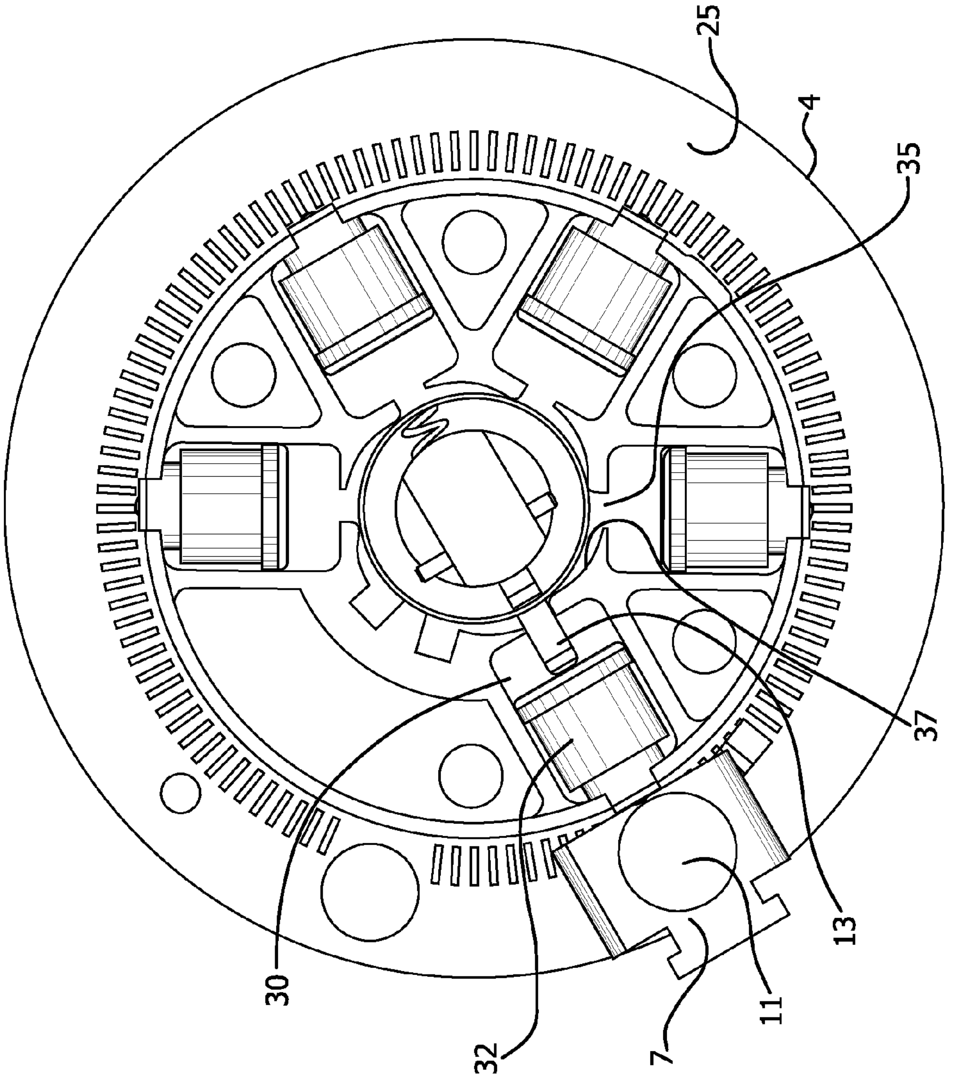
FIG. 15 is a perspective view of the operation of an embodiment of the self-contained assay device of the present invention.

Referring now to FIGS. 14 and 15, as soon as the rotation starts, ram pin 13 engages a cam surface 37 on cam plate 25. Ram pin 13 is contained until it reaches second opening 35 of the first of chambers 30. When ram pin 13 meets second opening 35 of the first of chambers 30, ram pin 13 thrusts outward towards piston and cylinder assembly 32 and the following actions occur. The force of ram pin 13 overcomes the force of light coil over spring 55 and the whole piston and cylinder assembly 32 moves forward and seals against small O-ring 12*b* on membrane housing block 7, which causes ball bearing 51 to move off its seat in piston 41. After breaking the ball bearing seal, ram pin 13 continues to apply force to cylinder 39 thus allowing reagent or wash solution 43 in cylinder 39 to escape into membrane housing block 7 through liquid inlet orifice 65 and onto membrane 11 where it has the opportunity to react with the specimen retained on membrane 11.

After the reaction, unbound specimen or reagent can pass through membrane 11 and deposit on absorbent blotter 24. The bound specimen or reagent, on the other hand, is immobilized by membrane 11 for a subsequent assay reaction.

At this point, assay device 10 is ready for the next operation which may comprise, for example, a wash or another assay. Button 8 is depressed thus engaging the trigger on ram pin 13 thus readying ram pin 13 for its next thrust when second housing 4 is rotated. Accordingly, the above steps are then repeated until ram pin 13 thrusts into the last of piston and cylinder assemblies 32 in the last of chambers 30 and comes to an end position. Thereby, the result of a previous reaction is made to react with the reagent and/or wash solution contained in piston and cylinder assembly 32 of a next chamber 30. In this way, the specimen is carried through a series of reactions in an analysis for detecting analyte(s) contained therein. The final result of the test can be easily observed through second housing 4 if transparent or via observation port 16. After the completion of the test, self-contained assay device 10 can be discarded and no cleaning step is necessary.

In a preferred embodiment, one or more of the piston and cylinder assemblies 32 containing a wash solution is or are used in self-contained assay device 10. In another preferred embodiment, a wash solution is arranged alternately with a reagent. Thereby, after each reaction of the reagent and the specimen, a wash solution is dispensed to wash away any unbound specimen or reagent. In this way, only the bound resultant is left on the membrane, which is to be used for the next reaction with the reagent in piston and cylinder assembly 32 of the next chamber 30. A reagent or wash solution may be the fluid contained in the first piston and cylinder assembly 32. In a preferred embodiment, a wash solution is contained in the first piston and cylinder assembly 32.

Figure 16:
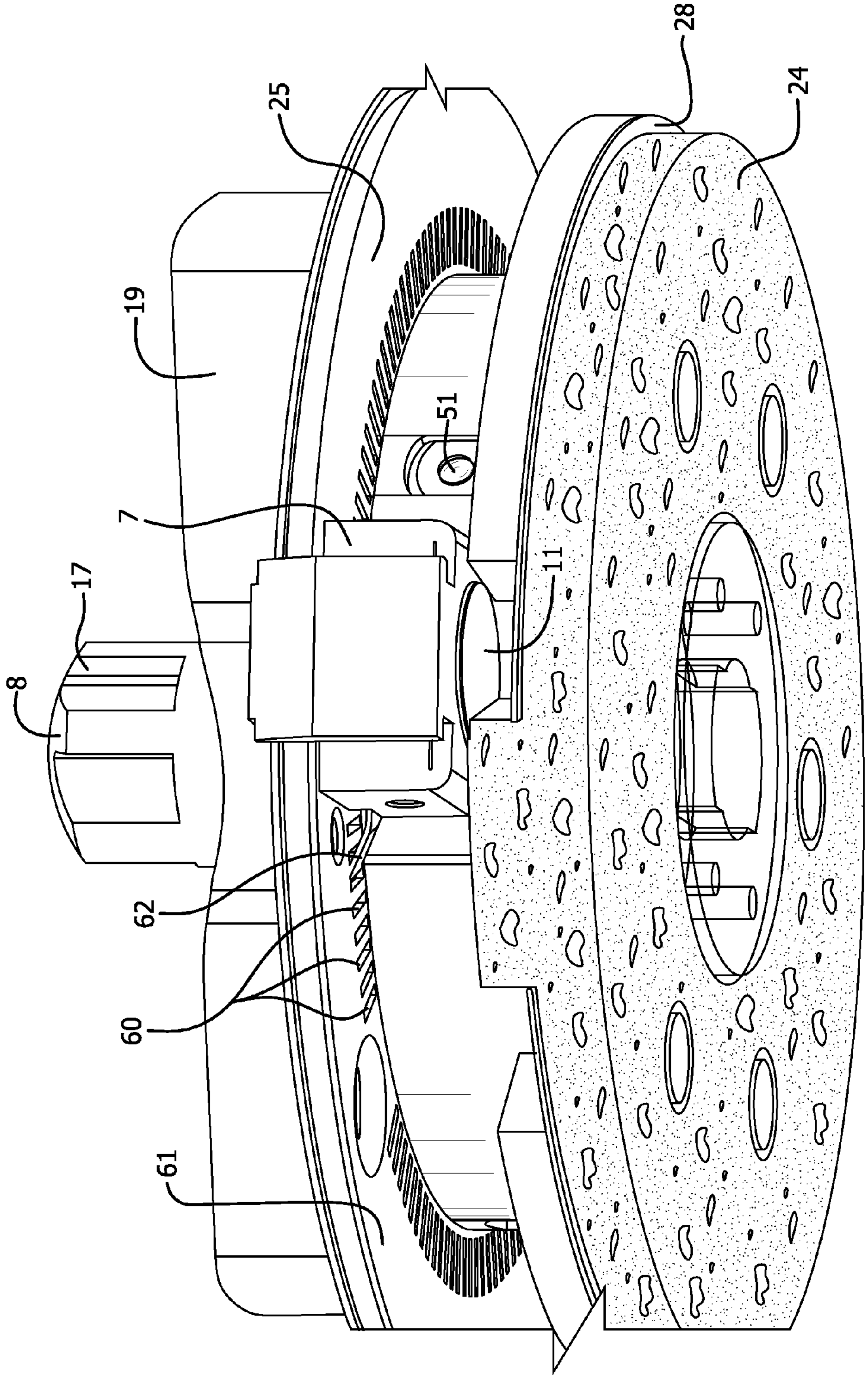
FIG. 16 is a perspective view of the operation of an embodiment of the self-contained assay device of the present invention comprising a mechanism that ensures one way rotation.

A preferred embodiment of the present invention is shown in FIG. 16 wherein structure is included to prevent two-way rotation of second housing 4. In FIG. 16, a ratchet mechanism is shown comprising a series of grooves 60 located radially around a perimeter portion 61 of the cam plate 25. Located on membrane housing block 7 is a tab 62 that fits within grooves 60. Tab 62 is angled such that counter-clockwise rotation of second housing 4 is prevented.

Assay device 10 of the present invention is useful to determine the presence (or absence) of an analyte in a sample or specimen suspected of containing the analyte. Any type of specimen or sample in fluid form can be used, including but not limited to biological samples such as blood, serum, plasma, milk, urine, sweat, saliva, cerebrospinal fluid, amniotic fluid, semen, vaginal and cervical secretions, bronchial secretions, intestinal fluid, wound fluid (exudates and transudates), thoracentesis fluid, cell or tissue suspensions, etc., environmental samples such as water samples, soil suspensions, etc.

As used according to the present invention, an analyte is intended to mean any compound or composition to be assessed which is a member of a specific binding pair and may be a ligand or a receptor. A member of a specific binding pair is one of two different compounds or compositions, having an area, either on the surface or in a cavity, which specifically binds to and is thereby defined as complementary with a particular spatial and polar organization of the other compound or composition. The members of a specific binding pair are generally referred to as "ligand" and "receptor" ("anti-ligand").

As used herein, a ligand includes any compound or composition for which a receptor naturally exists or can be prepared. Illustrative ligands include but are not limited to antigens; hormones; pheromones; signal substances such as neurotransmitters, signal proteins and peptides, etc.; enzyme substrates and cofactors; ligands for receptor proteins; nucleic acids and polynucleotides; biotin; lectins; growth factors or cytokines; drugs; toxins; etc.

As used herein, a receptor (anti-ligand) includes any compound or composition which recognizes a particular spatial and polar organization of a compound or composition, e.g., an epitopic or determinant site or a complementary binding site. Illustrative receptors include but are not limited to immunoglobulins or antibodies or antigen binding portions thereof such as Fv, $F(ab')_2$, Fab fragments, single chain antibodies, chimeric or humanized antibodies, complementary determining regions of antibodies; hormone receptors; pheromone receptors; signal substance receptors; enzymes; protein receptors; nucleic acids and polynucleotides; avidin or streptavidin; lectin binding proteins; growth factor or cytokine receptors; drug receptors; etc. As will be understood easily by those skilled in the art, nucleic acids, polynucleotides, and oligonucleotides which are complementary to one another can serve as the two members of a specific binding pair which can be used in assay device 10 of the present invention, one serving as ligand and the other serving as receptor or anti-ligand.

When the analyte to be detected is an antigen associated with an infectious agent such as a bacterium, fungus, virus, mycoplasma or other parasite, assay device 10 of the invention can be used for the detection of infectious disease in a patient from which the sample or specimen is obtained. When the analyte to be detected is an antibody against an antigen associated with an infectious agent, assay device 10 of the invention can be used to detect the presence of immunity to an infectious disease in the patient from whom the specimen is obtained. In this instance, the signal detected can be compared to a standard provided, and immunity is assessed by comparison to an appropriate signal, e.g., a color developed, indicating at least a minimum antibody titer present. In one embodiment, the standard can be provided as appropriate portion(s) 59*b* (see FIGS. 11*a*-11*c*) on membrane 11. The two above-described uses of the present device are only illustrative examples. Numerous other uses for the assay devices of the invention will occur to those skilled in the art depending upon the analyte to be detected, including but not limited to detection of the presence or absence of particular types of cancer, genetic mutations or defects, metabolic imbalances, drugs, toxins, pesticides, etc. and are all within the scope of the applications or methods for using the present invention.

The reagents and/or wash solutions, optionally including an ancillary material such as a buffer, stabilizer, additive to enhance binding, etc., contained in the assay device 10 as well as the amount of reagent retained in cylinder 39 of assay device 10 will depend upon the analyte to be detected and is readily known to those skilled in the art.

In all instances, there is at least one reagent which is complementary to and binds specifically to the analyte (one member of a specific binding pair) which is to be tested for in the assay, i.e., the other member of the specific binding pair.

In all instances, there is provided at least one or more of the reagents which provides a signal system, such as a color change, which indicates the presence of the analyte in the specimen being tested. One reagent which is a member of the specific binding pair which binds specifically to the analyte, i.e., second specific binding pair member, or another molecule which binds specifically to the second binding pair member is labeled to provide a signal system. Suitable signal systems employ the use of an enzyme label, a fluorescent label, a chemiluminescent label or enhanced chemiluminescent label, or a radioactive label, etc. Non-radioactive labels are preferred. Suitable signal systems are well-known to those skilled in the art. See, for example, David Wild, ed., *The Immunoassay Handbook*, Stockton Press, 1994, particularly at pages 63-77 (incorporated herein by reference) for suitable labels and signal generation systems useful when the specific binding pair members are antigen and antibody (or binding portion thereof). See, for example, George H. Keller et al., DNA Probes, Stockton Press, 1989, particularly at pages 71-148 (incorporated by reference herein) for suitable labels and signal generation systems when the specific binding pair members are complementary polynucleotides.

Preferred are signal systems in which a change, such as in color, indicating the presence of analyte in a specimen can be detected visually by the naked eye of the person using the assay device under normal ambient conditions. Alternatively, signal systems in which a change indicating the presence of analyte in a specimen can be detected using the naked eye of the person using the assay device aided by, for example, light of a particular wavelength, e.g., ultraviolet light, etc. or which can be detected using spectrophotometric or other instrumental detection systems can be used. Less preferred is a signal system using a radioactive label; in such instance an appropriate device for detecting emitted radiation is used.

In a preferred embodiment, the present invention employs a colloidal gold labeled ligand or antiligand reagent and ligand or antiligand bound solid phase particles as a detection means as described in U.S. Pat. No. 4,853,335, the disclosure of which is herein incorporated by reference in its entirety.

In another preferred embodiment, fluorescent detecting reagents are employed in the assay device 10 of the present invention. Such detection means require a light source to excite the fluorochrome and detect the bound reagent.

As one illustrative example, when the analyte to be detected is an antigen suspected of being present in a patient specimen, the reagents retained in assay device 10 can include a capture anti-antigen antibody bound to the reaction membrane member; a second anti-antigen antibody that recognizes a different epitope from that recognized by the capture antibody labelled, e.g., with an enzyme such as horseradish peroxidase; a wash solution; and a substrate for the enzyme label, e.g., 2,2'-azino-bis(ethylbenzothiazoline-6-sulfonate) (ABTS), D-phenylenediamine (OPD) or (3,3',5,5'tetramethyl benzidine (TMB) (all peroxidase substrates). Alternatively, the reagents for such assay can include a capture antibody; an anti-antigen antibody; a wash solution; an anti-antibody labelled e.g., with an enzyme; a wash solution; and a substrate for the enzyme label.

As another illustrative example, when the analyte to be detected is an antibody suspected of being present in a patient specimen, the reagents retained in the assay device 10 can include an antigen (to which the suspected antibody binds specifically) bound to the reaction membrane member; an anti-immunoglobulin, e.g., human immunoglobulin; an antibody labeled, e.g., with an enzyme label; a wash solution; and a substrate for the enzyme label which when reacted with the enzyme provides a detectable color change indicating presence of the analyte.

According to an embodiment of the present invention, illustrated in FIG. 11*a*, a predetermined amount of the analyte to be detected is immobilized on a predetermined portion 59*b* of membrane 11. The predetermined amount of immobilized analyte reacts with all the reagents and affords a positive analyte control that provides a positive control signal indicating that the reagents are functioning properly and assuring the user of the device that the assay has been successfully conducted.

The following illustrative example describes a method for detecting an analyte which is an antigen, e.g. a hepatitis A antigen, suspected of being present in a patient using the self-contained assay device 10 of the present invention. The example is for illustrative purposes only and is in no way intended to limit the scope of the methods of the invention or the appended claims. As will be appreciated by those skilled in the art, the methods for using the self-contained assay device 10 can be modified or changed for use to assay for numerous other analytes and all such modifications or changes may be practiced and are encompassed within the scope of the appended claims.

As an example, the method for detecting hepatitis antigen comprises first introducing a predetermined quantity of a specimen which is a patient blood sample into self-contained assay device 10 of the present invention through opening 22 on second housing 4 which contains a filter member for removing particulates, assay device 10 having a number of reagents immobilized onto separate portions 59*b* of membrane 11 positioned in membrane housing block 7 onto which the blood sample is introduced. Membrane 11 at specific areas and zones of portion 59*b* has immobilized thereon the following substances: hepatitis A viral antigen (positive control), unrelated protein such as gelatin (negative control), anti-hepatitis A antibody (capture antibody), anti-hepatitis C antibody, and anti-hepatitis B antibody. The method next comprises rotating second housing 4 relative to membrane housing block 7 as detailed above to dispense a wash solution to wash away any unbound material. Second housing 4 is rotated relative to membrane housing block 7 to dispense a next reagent containing an anti-hepatitis A antibody that recognizes an epitope different from the one recognized by the capture antibody, labeled with an enzyme label. The released antibody is permitted to contact the specimen on membrane 11 for a sufficient time so that any antigen present can bind to the enzyme labeled antibody. Second housing 4 is rotated again relative to membrane housing block 7 to dispense a wash solution. The above steps are repeated until second housing 4 reaches the next chamber 30 and dispenses a reagent retained therein releasing a substrate for the enzyme (label) and permitting reaction to occur between any enzyme labeled antibody bound to membrane 11 and the enzyme substrate to provide a color change indicative of the presence of antigen. Second housing 4 is rotated relative to membrane housing block 7 to move from the last chamber 30 to an end position. Finally, the method comprises observing the results and comparing the color signal developed on the portion of membrane 11 to which the specimen was applied with that of the portion 59*b* of membrane 11 on which hepatitis A was immobilized as a positive control to determine whether hepatitis A is present in the patient sample.

In another embodiment, self-contained assay device 10 can be used to detect the presence of more than one analyte in a sample. In a preferred mode of this embodiment of the invention, assay device 10 can be used to detect the presence of a number of antibodies to a number of infectious agents to assess whether a patient has sufficient immunity to each of the various infectious agents.

As an illustrative example, the assay device 10 can be used to detect antibodies against a panel of viral agents, e.g., measles, mumps and rubella, etc. in order to assess the status of vaccination against each such virus. A sufficient amount of specimen is applied to wet or to cover membrane 11. Membrane 11 at specific areas or zones of portions 59*b* contains the following substances: human serum immunoglobulins (positive control), gelatin, an unrelated protein (negative control), measles antigen, mumps antigen, and rubella antigen, respectively. As will be understood by those skilled in the art, the position and/or configuration of each of the positive and negative controls and of each of the antigens on the membrane member is identified to help easily determine which one or more antibodies is/are present in the specimen. See, for example, FIGS. 11*a*-11*c*. The specimen is permitted to contact membrane 11 for a time sufficient for any antibody in the specimen to bind to the immobilized antigen(s). The first chamber 30 retains wash solution to wash away any unbound antibody. The next chamber 30 retains anti-human immunoglobulin labeled with an enzyme label. The next chamber 30 retains a wash solution to wash away any unbound labeled antibody. The next chamber 30 retains enzyme substrate, which provides a color change when reacted with enzyme (labeled antibody). Thus, when the assay is completed, visualization of the results is easily provided to determine the presence or absence of each of measles, mumps, and rubella antibodies in the patient specimen.

The foregoing description is only illustrative of the principle of the present invention. It is to be recognized and understood that the invention is not to be limited to the exact configuration as illustrated and described herein. Accordingly, all expedient modifications readily attainable by one versed in the art from the disclosure set forth herein that are within the scope and spirit of the present invention are to be included as further embodiments of the present invention. The scope of the present invention accordingly is to be defined as set forth in the appended claims.

What is claimed is:

1. A self-contained assay device for detecting analyte(s) in a specimen comprising:

a first housing having a bottom and a raised wall;

a button tower centrally secured to the bottom of the first housing, the button tower including:

a base having a spring-loaded ram pin;

a button engaging a trigger to retract the ram pin within the base member, the button having a plurality of cut-out portions;

a membrane housing block fixedly fit in a position on the raised wall of the first housing and having an opening configured to receive a liquid specimen, the membrane housing block including a porous membrane on a bottom portion, a liquid inlet orifice in a position facing the button tower, and a liquid-tight seal surrounding the opening;

an absorbent blotter located adjacent to the bottom of the first housing, the absorbent blotter having a raised portion located in a position under the membrane housing block;

a blotter barrier plate located on a surface of the blotter opposite the bottom of the first housing;

a second housing adapted to be fixedly fit in the first housing, the second housing including:

a top surface having a handle portion and a center hole for receiving the button;

a rim portion defining an outer end wall and a plurality of chambers, wherein each chamber has a first opening located at the outer end wall for communicating with the membrane housing block and a second opening located at an inner portion of the chamber opposite the first opening, wherein each chamber has at least one cam-shaped surface adjacent to the second opening, and wherein each chamber has a cylinder and piston assembly secured to the chamber by a coil-over spring, the cylinder and piston assembly retaining a reagent or wash solution, wherein the piston includes a channel comprising a vented set screw, a ball bearing, and a spring acting on the ball bearing to seal an outer end of the channel to provide a liquid-tight reservoir for the reagent or wash solution, wherein, when the button is depressed, the second housing is able to rotate relative to the membrane housing block thus causing the ram pin to engage one of the cam surfaces of the rim portion of the second housing to contain the ram pin until it reaches the second opening in one of the chambers thus causing the ram pin to thrust into the cylinder to move the cylinder and piston assembly, opposite the force of the coil-over spring, against the liquid inlet orifice on the membrane housing block thus moving the ball bearing to break the seal and allow the reagent or wash solution to escape into the membrane housing block and onto the membrane.

2. The assay device of claim 1 wherein the button further has a spring pin located in the handle portion such that the button, when depressed, is held down by the spring pin in the handle portion via the cut-out portions.

3. The assay device of claim 1 wherein the membrane housing block further comprises an O-ring on a top surface to create a liquid tight seal between the membrane housing block and the second housing.

4. The assay device of claim 1 wherein the absorbent blotter is a sponge.

5. The assay device of claim 1 wherein the ball bearing is held inside the channel by an internal lip and by force of the spring.

6. The assay device of claim 1 comprising a total of five chambers.

7. The assay device of claim 1 further comprising a ratchet mechanism for preventing two-way rotation.

8. The assay device of claim 7 wherein the ratchet mechanism comprises a tab acting against a groove in the rim portion of the second housing.

9. The assay device of claim 1 wherein the trigger to retract the ram pin within the base member comprises an angled slot.

10. The assay device of claim 1 further comprising a mesh structure supporting the membrane and located between the raised portion of the blotter member and the membrane.

11. The assay device of claim 1 wherein the second housing further comprises an observation window.

12. The assay device of claim 1 wherein the second housing further comprises an opening through which a predetermined quantity of a specimen can be added.

13. A self-contained assay device for detecting analyte(s) in a specimen comprising:

a first housing having a bottom and a raised wall;

a button tower centrally secured to the bottom of the first housing, the button tower including:

a base having a spring-loaded ram pin;

a button engaging a trigger to retract the ram pin within the base, the button having a plurality of cut-out portions;

a membrane housing block fixedly fit in a position on the raised wall of the first housing and having an opening configured to receive a liquid specimen, the membrane housing block including a porous membrane on a bottom portion, a liquid inlet orifice in a position facing the button tower, and a liquid-tight seal surrounding the opening;

a second housing adapted to be fixedly fit in the first housing, the second housing including:

a top surface having a handle portion and a center hole for receiving the button;

a rim portion defining an outer end wall and a plurality of chambers, wherein each chamber has a first opening located at the outer end wall for communicating with the membrane housing block and a second opening located at an inner portion of the chamber opposite the first opening, wherein each chamber has at least one cam-shaped surface adjacent to the second opening, and wherein each chamber has a cylinder and piston assembly secured to the chamber by a coil-over spring, the cylinder and piston assembly retaining a reagent or wash solution, wherein the piston includes a channel comprising a vented set screw and a spring acting on a ball bearing to seal an outer end of the channel to provide a liquid-tight reservoir for the reagent or wash solution, wherein, when the button is depressed, the second housing is able to rotate relative to the membrane housing block thus causing the ram pin to engage one of the cam surfaces of the rim portion of the second housing to contain the ram pin until it reaches the second opening in one of the chambers thus causing the ram pin to thrust into the cylinder to move the cylinder and piston assembly, opposite the force of the coil-over spring, against the liquid inlet orifice on the membrane housing block thus moving the ball bearing to break the seal and allow the reagent or wash solution to escape into the membrane housing block and onto the membrane.

14. The assay device of claim 13 further comprising an absorbent blotter located adjacent to the bottom of the first housing, the absorbent blotter including a raised portion located in a position under the membrane housing block.

15. The assay device of claim 14 further comprising a blotter barrier plate located on a surface of the blotter opposite the bottom of the first housing.

16. A method for detecting analyte(s) in a specimen comprising the steps of:

adding a specimen of a predetermined quantity into the self-contained assay device of claim 14 through an opening on the second housing;

depressing the button and rotating the second housing relative to the membrane housing block causing the ram pin to engage one of the cam surfaces of the rim portion of the second housing to contain the ram pin until it reaches the second opening in one of the chambers thus causing the ram pin to thrust into the cylinder to move the cylinder and piston assembly, opposite the force of the coil-over spring, against the liquid inlet orifice on the membrane housing block thus moving the ball bearing to break the seal and allow the reagent or wash solution to escape into the membrane housing block and onto the membrane;

repeating the above step until the ram pin thrusts into a last cylinder and piston assembly to dispense the reagent or wash solution contained therein; and observing the results.

17. The assay device of claim 1 wherein a gold labeled ligand or antiligand reagent and ligand or antiligand bound solid phase particles are employed as a detection means.

18. The assay device of claim 13 wherein a gold labeled ligand or antiligand reagent and ligand or antiligand bound solid phase particles are employed as a detection means.

* * * * *